US008603039B2

(12) United States Patent
Brand

(10) Patent No.: US 8,603,039 B2
(45) Date of Patent: Dec. 10, 2013

(54) SYRINGE PROTECTOR

(76) Inventor: Christopher Brand, Muncie, IN (US)

(*) Notice: Subject to any disclaimer, the term of this patent is extended or adjusted under 35 U.S.C. 154(b) by 469 days.

(21) Appl. No.: 12/363,733

(22) Filed: Jan. 31, 2009

(65) Prior Publication Data

US 2010/0081998 A1 Apr. 1, 2010

Related U.S. Application Data

(63) Continuation-in-part of application No. 11/276,623, filed on Mar. 8, 2006, now abandoned.

(60) Provisional application No. 60/659,686, filed on Mar. 8, 2005.

(51) Int. Cl.
A61M 5/32 (2006.01)
A61M 5/00 (2006.01)
B65D 83/10 (2006.01)

(52) U.S. Cl.
USPC ............ 604/192; 604/263; 604/110; 206/365

(58) Field of Classification Search
USPC ............ 604/162, 164.08, 171, 192, 193, 197, 604/198, 263; 206/365–366, 354–359
See application file for complete search history.

(56) References Cited

U.S. PATENT DOCUMENTS

| | | | |
|---|---|---|---|
| 268,996 A | 12/1882 | Brinkerhoff | |
| 2,367,703 A * | 1/1945 | Vaughan | 279/2.03 |
| 3,052,241 A * | 9/1962 | Myerson et al. | 604/192 |
| 3,063,450 A * | 11/1962 | Myerson et al. | 604/218 |
| 3,434,473 A | 3/1969 | Smith | |
| 3,853,010 A | 12/1974 | Christen et al. | |
| 4,631,057 A | 12/1986 | Mitchell | |
| 4,693,708 A | 9/1987 | Wanderer et al. | |
| 4,723,943 A | 2/1988 | Spencer | |
| 4,799,927 A * | 1/1989 | Davis et al. | 604/192 |
| 4,840,185 A | 6/1989 | Hernandez | |
| 4,908,023 A | 3/1990 | Yuen | |
| 4,923,445 A | 5/1990 | Ryan | |
| 4,973,315 A | 11/1990 | Sincock | |
| 4,986,817 A * | 1/1991 | Code | 604/192 |
| 4,998,920 A | 3/1991 | Johnson | |
| 5,021,047 A | 6/1991 | Movern | |
| 5,041,099 A | 8/1991 | Gelabert | |
| 5,078,695 A | 1/1992 | Farrar et al. | |
| 5,085,647 A | 2/1992 | Henderson et al. | |
| 5,092,462 A | 3/1992 | Sagstetter et al. | |
| 5,209,738 A * | 5/1993 | Bruno | 604/192 |
| 5,259,840 A | 11/1993 | Boris | |
| 5,334,151 A | 8/1994 | Santilli | |

(Continued)

FOREIGN PATENT DOCUMENTS

GB 2198644 6/1987
WO 2005041846 5/2005

Primary Examiner — Kevin C Sirmons
Assistant Examiner — William Carpenter
(74) Attorney, Agent, or Firm — Ice Miller, LLP

(57) ABSTRACT

A syringe protector. The syringe protector includes a clamping member, a guard member, and a retaining member. The clamping member being able to lockably engage the needle guard and allow the passage of a needle therethrough. Insertion of the clamping member into the guard member creates a locking interaction between the toothed surface of the clamping member and a complementary toothed or ribbed surface of the guard member. Further, the clamping member holds a retaining member which acts to secure a syringe body once the needle of the syringe enters the guard member.

20 Claims, 20 Drawing Sheets

(56) References Cited

U.S. PATENT DOCUMENTS

| | | | |
|---|---|---|---|
| 5,347,078 A * | 9/1994 | Eckels | 588/249.5 |
| 5,395,338 A | 3/1995 | Gaba | |
| 5,403,288 A | 4/1995 | Stanners | |
| 5,519,931 A | 5/1996 | Reich | |
| 5,582,594 A | 12/1996 | Chen | |
| 5,593,391 A | 1/1997 | Stanners | |
| 5,697,908 A | 12/1997 | Imbert et al. | |
| 5,718,689 A * | 2/1998 | Stevenson | 604/192 |
| 5,725,503 A | 3/1998 | Arnett | |
| 5,941,857 A | 8/1999 | Nguyen et al. | |
| 6,036,675 A | 3/2000 | Thorne et al. | |
| 6,287,282 B1 | 9/2001 | Bonaldo et al. | |
| 6,585,702 B1 | 7/2003 | Brunel | |
| 2004/0010227 A1 | 1/2004 | Riesenberger et al. | |

* cited by examiner

SYRINGE PROTECTOR

CROSS REFERENCE TO RELATED APPLICATIONS

This continuation-in-part application claims priority to U.S. Utility patent application Ser. No. 11/276,623 filed Mar. 8, 2006 now abandoned, which claims the benefit of U.S. Provisional Patent Application Ser. No. 60/659,686 filed Mar. 8, 2005, both of which are incorporated herein by reference.

FIELD

The present disclosure relates generally to syringes, and more particularly to devices for protecting the needle end of conventional medical syringes so as to prevent accidental needle pricks.

BACKGROUND

As commonly known in the art, syringes are medical devices used to inject fluids into a body and/or withdraw fluids from within a body or its cavities. Conventional medical syringes typically include a barrel portion with one end configured to mate with a conventional piercing element, such as a pointed hollow needle or cannula. A plunger rod is inserted through the opposing end of the barrel portion. By engaging the plunger rod with an elastomeric stopper element fitted in a fluid-tight manner within the interior of the barrel, a user can apply manual force to the plunger to either withdraw or deliver the syringe contents.

During use, it is not uncommon for the needle portions to be involved in accidental needle sticks or punctures. Such puncture incidents can pose a great health risk to medical personnel via the accidental transmission of pathogens and/or pharmacological substances. Thus, it is of utmost importance to provide protection for medical personnel from pathogen-contaminated blood, body fluids, and/or pharmacological substances still present in or on the syringe needle.

Immediately following use of a syringe, a syringe protector can be positioned over the needle cannula, thus preventing an accidental needle prick. A syringe protector should remain permanently affixed to the syringe in order to provide the highest degree of protection in the handling and disposal of the used syringe. Further, as medical syringes are frequently used during times of emergency or high stress, it is highly desirable that a syringe protector be simple to use and be composed of few pieces in order to be most easily employed. Finally, due to the high volume of syringes used daily in hospitals, laboratories, clinics and residential homes, the components of a syringe protector should be easily and inexpensively formed by mass production.

Previous syringe protectors have failed to meet these criteria. Existing syringe protectors are typically composed of numerous small pieces, do not permanently occlude the needle portion of a syringe, and/or are not readily compatible with a conventional medical syringe. There is a need for a syringe protector which is easily and permanently affixed to a conventional medical syringe without special tools, especially during times of high stress and relative inattention such as during emergencies. There also exists a need for a syringe protector that is comprised of a minimal number of parts which are easily formed using mass production techniques. Various aspects of the present disclosure address these needs.

SUMMARY

The present disclosure includes disclosure of embodiments of a syringe protector. According to at least one embodiment of the present disclosure, a syringe protector for enclosing a needle portion of a syringe comprises a clamping member having a toothed surface, a base wall, a first axial passage, a second axial passage adapted to receive a syringe therethrough, and at least one flexible flange, wherein the at least one flexible flange defines the first axial passage and the base wall defines the second axial passage; a retaining member having a retaining wall defining an opening, the retaining wall having at least one protrusion, wherein the retaining member is operably connected to the clamping member; and a needle guard having a toothed surface, wherein an interaction between the toothed surface of the clamping member and the toothed surface of the guard member securably engages the clamping member and the guard member, and wherein the retaining wall of the retaining member compressively grips a syringe inserted through the opening of the retaining member.

According to at least one aspect of the present disclosure, the toothed surface of the clamping member is an exterior surface and the toothed surface of the needle guard is an interior surface.

According to at least one aspect of the present disclosure, the syringe comprises a body having a needle attached to one end thereof, and the needle guard comprises a stop member configured and arranged so as to allow the needle to pass therethrough and to prevent the body from passing therethrough.

According to at least one aspect of the present disclosure, at least one protrusion of the retaining member is oriented away from the first axial opening.

According to at least one aspect of the present disclosure, the retaining member is operably connected to the clamping member between the first axial passage and the second axial passage. According to at least one aspect of the present disclosure, the retaining member is operably connected to the clamping member within the clamping member.

According to at least one aspect of the present disclosure, the needle guard further comprises an upper edge and an internal surface between the upper edge and the toothed surface, the internal surface having a first diameter adjacent to the upper edge and a second diameter adjacent to the toothed surface, the first diameter being larger than the second diameter.

According to at least one aspect of the present disclosure, at least one flexible flange comprises a shoulder, the shoulder abutting the internal surface of the needle guard.

According to at least one aspect of the present disclosure, the needle guard further comprises a cavity, the cavity sized to receive a needle portion of the syringe therein.

According to at least one aspect of the present disclosure, a syringe protector further comprises a cap connected to the needle guard, the cap comprising an upper rim defining a first opening, and lower rim defining a second opening, and a continuous cap surface between the upper rim and lower rim.

BRIEF DESCRIPTION OF THE DRAWINGS

The features and advantages of this disclosure, and the manner of attaining them, will be more apparent and better understood by reference to the following descriptions of the disclosed methods and systems, taken in conjunction with the accompanying drawings, wherein.

DESCRIPTION OF SELECTED EMBODIMENTS

Figure 1:
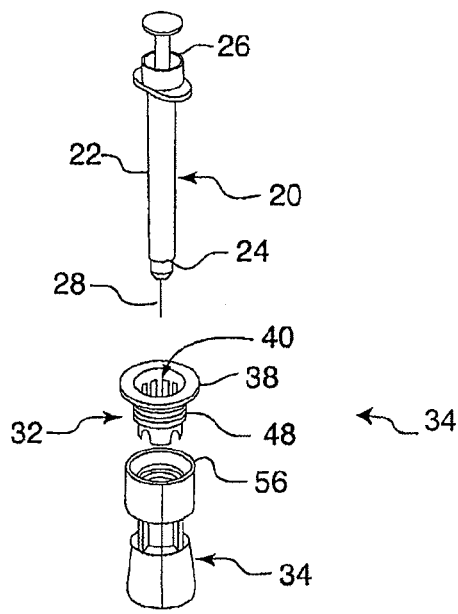
FIG. 1 is an exploded, perspective view of a syringe protector with a conventional medical syringe according to at least one embodiment.
Figure 2:
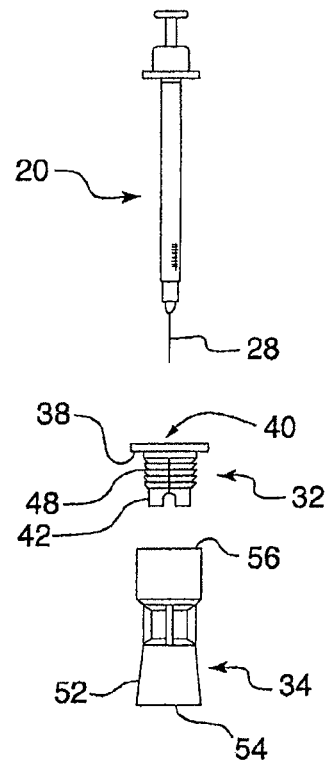
FIG. 2 is an exploded, plan view of the syringe protector and syringe of FIG. 1 according to at least one embodiment.

For the purposes of promoting an understanding of the principles of the disclosure and presenting its currently understood best mode of operation, reference will now be made to the embodiments illustrated in the drawings and specific language will be used to describe the same. It will nevertheless be understood that no limitation of the scope of the disclosure is thereby intended, with such alterations and further modifications in the illustrated device and such further applications of the principles of the disclosure as illustrated therein being contemplated as would normally occur to one skilled in the art to which the disclosure relates.

Medical syringes are manufactured in a variety of styles and sizes and utilize various needle lengths. A conventional syringe 20 such as those used subcutaneously for the delivery of pharmacological preparations or the withdrawal of blood or other fluids, includes an integrally formed cylindrical housing 22, a gripping collar, a nozzle end 24 and an open end 26. The housing is typically formed for a type of polypropylene plastic. The syringe further includes a movable plunger having a gripping collar, a stem, and an elastomeric stopper. The plunger is inserted through the open end of the cylindrical housing such that the stopper forms a movable seal within the housing. By moving the plunger into the housing, fluid in the syringe is expelled through the nozzle end. Alternatively, by drawing an inserted plunger partially out from the housing a negative pressure is generated within the body of the syringe so as to draw fluid into the cylindrical housing through the nozzle end. A cannular needle 28 is fixably or removably mounted to the syringe such that fluid passing through the nozzle end also passes through the cannula of the needle.

The length and diameter of syringes and their needles vary according to the intended application. Syringes for applications such as subcutaneous insulin injection are typically less than 0.25 inches in diameter and have small needles such as a 0.5 inch long, 28 gauge diameter needle. Syringes for intramuscular injections are typically 0.25-0.5 inches in diameter and have larger needles such as a 1.5 inch long, 21 gauge diameter needle. Even larger syringes are designed for specialized applications and procedures. Still other syringe designs include Luer or Luer-Lok type syringes which have needles that are threaded onto the syringe body.

The following discussion refers to the structure and operation of a variety of syringe protectors with respect to a conventional medical syringe 20. It is understood that syringe protectors sized and adapted to accommodate non-standard syringes are also contemplated. Although the following discussion refers only to syringes, other embodiments of syringe protectors described herein may be used to secure other types of sharp medical instruments such as lancets, glucometer sticks, and the like until disposal. The syringe protectors are typically constructed out of polypropylene, although other plastics, composites and suitable materials may also be used.

Turning now to the drawings, FIGS. 1-7 show at least one embodiment of syringe protector 30. Syringe protector 30 comprises a clamping member 32 and a needle guard 34. Clamping member 32 is ferrule-shaped in this particular embodiment and includes a toothed exterior surface 36, a flexible flange 38 defining an axial opening 40, and at least one flexible flange portion or member 42 extending from flexible flange 38 and defining a flexible locking means. In this particular embodiment, clamping member 32 is shown with four (4) flexible flanges. This is for illustrative purposes only and other embodiments have a greater or lesser number of flexible flanges. Optionally, the wall 44 of axial opening 40 includes one or more ribs or ridges 46 configured and arranged so as to be substantially parallel to the direction of axial opening 40. In other embodiments, one or more ribs or ridges are configured in orientations other than substantially parallel to the direction of the axial opening. Flange members 42 further include a toothed exterior surface 48 and a leading surface edge 50. In other embodiments, the clamping member is configured in other suitable shapes such as square, octagonal, and the like.

Figure 3:
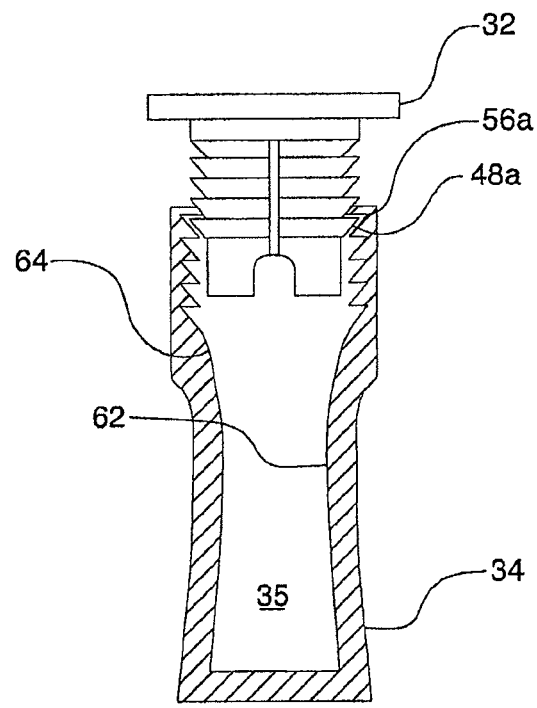
FIG. 3 is a plan view of a partial cross-section of the syringe protector of FIG. 1 according to at least one embodiment.
Figure 4:
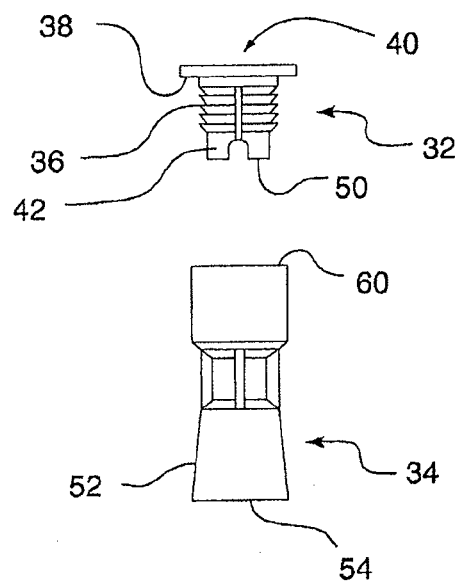
FIG. 4 is an exploded, plan view of the syringe protector of FIG. 1 according to at least one embodiment.
Figure 5:
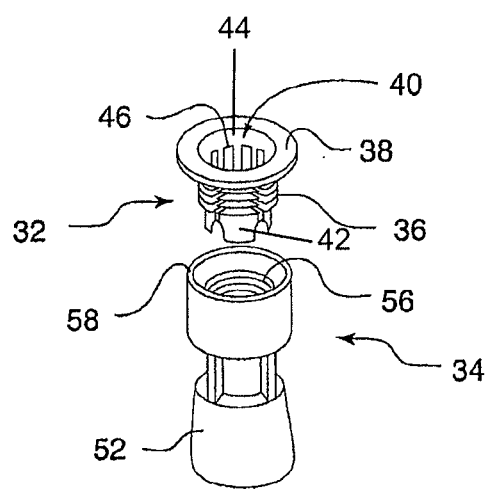
FIG. 5 is an exploded, perspective view of the syringe protector of FIG. 1 according to at least one embodiment.
Figure 6:
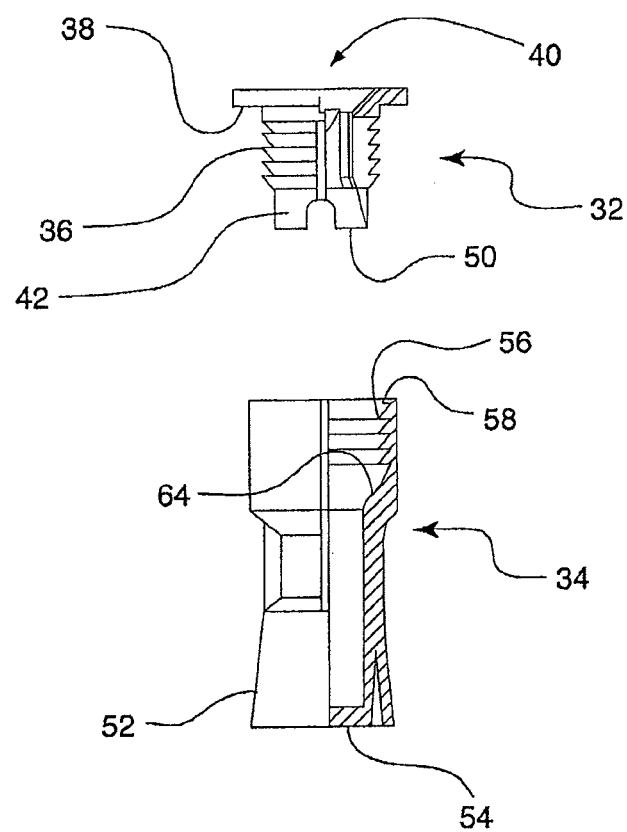
FIG. 6 is an exploded, plan view of a partial cross-section of the syringe protector of FIG. 1 according to at least one embodiment.

Needle guard 34 is generally tubular-shaped defining a cavity 35 and includes a flared base 52 having a generally flat bottom surface 54, a toothed interior surface 56, and a generally annular rim 58 adjacent to an upper edge 60. In this particular embodiment, all chamfers of toothed surface 48 of clamping member 32 and of toothed surface 56 of guard member 34 are disposed at approximately a 45 degree angle relative to the sides of clamping member 32 and guard member 34, respectively. Toothed interior 48 and toothed exterior 56 are configured and arranged such that when clamping member 32 is inserted into guard member 34, interaction between the toothed surfaces locks the two members together as shown in FIG. 3. In one embodiment, syringe protectors 30 are provided in a "pre-loaded" configuration where at least the first tooth 48a of clamping member 32 and the first tooth 56a of guard member 34 are engaged.

Figure 7:
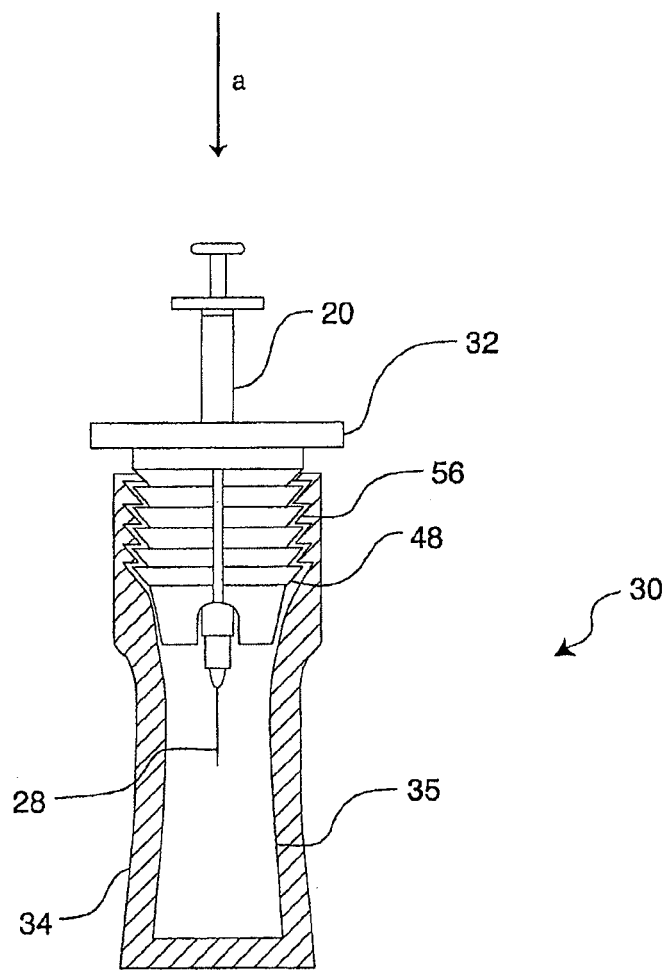
FIG. 7 is a plan view of a partial cross-section of a syringe protector engaged with a syringe according to at least one embodiment.

Continuing with the present embodiment, the interior diameter of the axial passage 40 of clamping member 32 is sized such that it receives the nozzle end 24 of a syringe 20 therethrough. The interior surface 62 of needle guard 34 is provided with a sloped deflecting surface 64 defined by a cross-sectional area of decreasing diameter arranged between base 54 and toothed surface 56. Sloped deflecting surface 64 abuttingly deflects leading surface 50 of flange portions 42 of clamping member 32 to force or deflect the flange portions radially inward as syringe clamping member 32 is urged downward in the direction indicated by arrow "a" into needle guard 34 as shown in FIG. 7. Urging clamping member 32 into needle guard 34 also serves to deflect flange portions 42 radially inward and compressibly engages and locks nozzle end 24 of syringe 20 in syringe guard 30. When syringe 20 is engaged and locked in syringe guard 30, needle 28 is protectively surrounded by needle guard 34, thereby preventing accidental needle sticks until the syringe and guard combination is properly disposed of using mechanical shredding, incineration, and/or other suitable disposal means.

Figure 8:
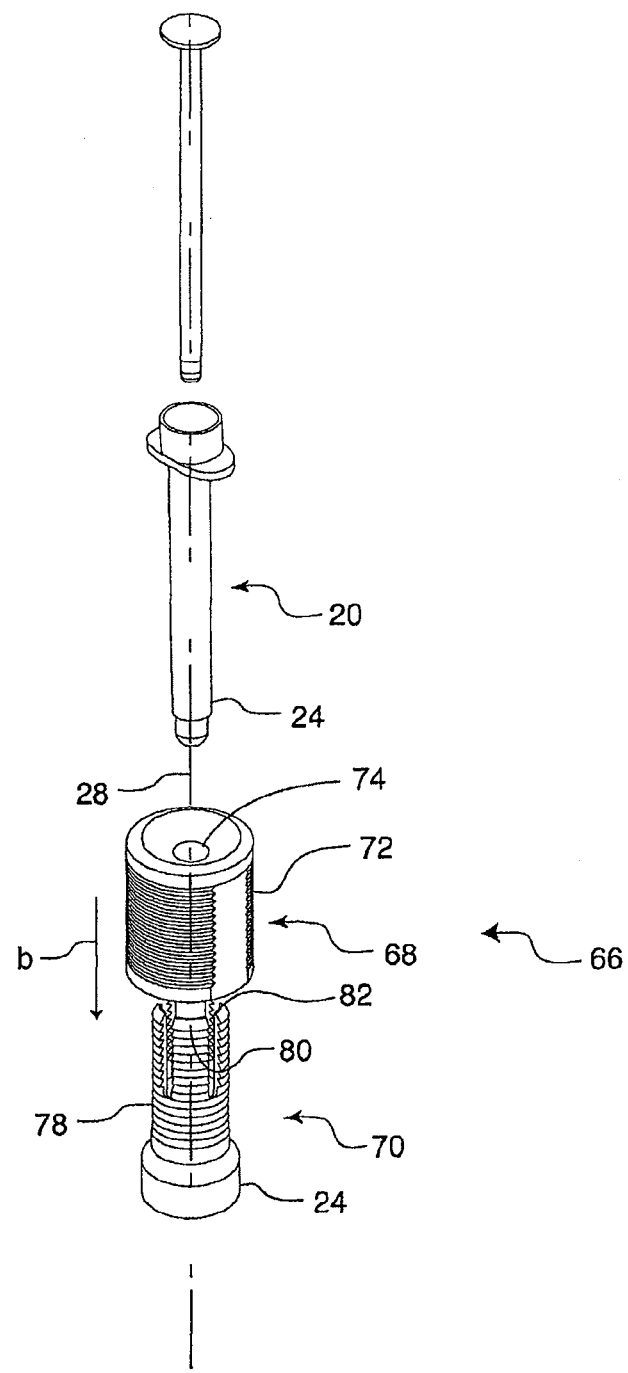
FIG. 8 is an exploded, perspective view of a syringe protector with a medical syringe according to at least one embodiment.

Another embodiment of a syringe protector is shown in FIG. 8. In this particular embodiment, protector 66 includes a clamping or actuating member 68 and a guard member 70. Actuating member 68 is shown as generally cylindrical in shape for illustrative purposes only. In other embodiments, alternative actuating member configurations such as those with square or octagonal cross-sections are also suitable. Actuating member 68 includes a cover portion 72, an axial opening 74, a toothed or ribbed inner surface (not shown) similar to the toothed surface of guard member 34 previously discussed with respect to FIGS. 1-7, and a camming or deflecting surface similar to surface 64 in FIGS. 1-7.

Guard member 70 is generally cylindrically shaped in this particular embodiment with a flared base portion 76 to provide stability when protector 66 is placed upon a flat surface. Guard member 70 is further provided with a toothed exterior surface 78 and at least one flexible flange portions 80. In this embodiment, guard member 70 is shown with four (4) flexible flange members. This is for illustrative purposes only and other embodiments will have a greater or lesser number of flange members. The toothed surfaces of actuator 68 and guard 70 are configured and adapted so as to cooperate in a ratcheting fashion when actuator 68 is urged over guard 70. In another embodiment, a syringe guard is provided in a pre-assembled state prior to actual use, wherein the actuator is provided disposed downward onto the needle guard, initiating a ratchet engagement between at least the first teeth of the toothed surfaces of the actuator member and the guard member.

Continuing with FIG. 8, a conventional medical syringe 20 is placed within axial passageway 74 of the actuator 68 by the user such that the needle 28 of syringe 20 extends downwardly into the interior cavity 82 of guard 70. Downward pressure exerted by the user on actuator 68 and syringe 20 urges actuator 68 in the direction indicated by arrow "b", whereby the internal camming surface of actuator 68 abuttingly engages and deflects flanges 80 radially inward. The radial deflection of flanges 80 compressibly clamps and locks the distal end 24 of syringe 20 thereby permanently enclosing needle 28 within cavity 82 so as to prevent accidental needle pricks.

Figure 9:
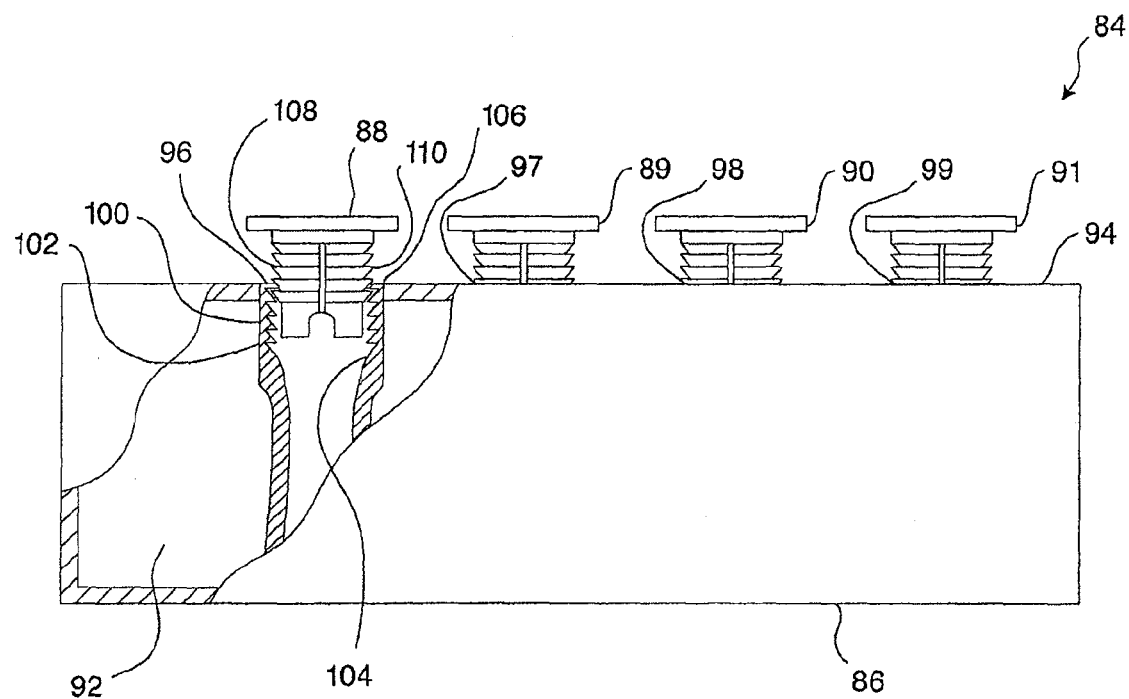
FIG. 9 is a side plan view of a partial cross-section of a syringe protector according to at least one embodiment.

A side plan view of a partial cross-section of yet another embodiment of a syringe protector 84 is shown in FIG. 9. In this particular embodiment, syringe protector 84 comprises a box or tray 86 and a plurality of clamping members 88-91. Tray 86 is shown as a box having a cavity 92 bounded on one side by a substantially flat surface 94 having a plurality of locking site openings 96-99. In this particular embodiment, tray 86 includes four locking sites, but trays having a greater of lesser number of locking sites are also contemplated. Locking site 96 includes a toothed surface 100 having a plurality of teeth or ridges 102 and a sloped camming or deflecting surface 104. In this particular embodiment, locking sites 96-99 are sized and adapted to accept clamping members of similar size and configuration. In other embodiments, the tray includes locking sites configured and adapted to accept clamping members designed to clamp and hold syringes of different sizes and/or configurations.

Continuing with FIG. 9, clamping members 88-91 are similar in structure and operation to clamping member 32 as previously described with respect to FIGS. 1-7. Clamping member 88 includes at least one flexible flange 106 and a toothed or ridged surface 108 having a plurality of teeth 110 configured and arranged such that when clamping member 88 is inserted into locking site 96, interaction between the toothed surfaces locks clamping member 88 to locking site 96 and tray 86. Inserting a syringe through clamping member 88 and urging clamping member 88 down into locking site 96 causes camming surface 104 to abuttingly deflect flange 106 radially inward so as to compressively grip the syringe so that the needle portion of the syringe is safely disposed within cavity 92 of tray 86.

Figure 10:
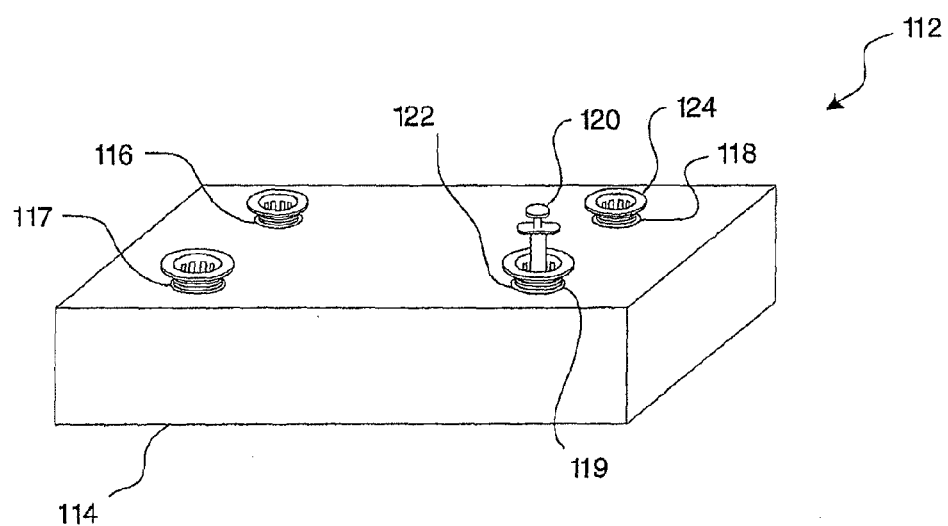
FIG. 10 is a perspective view of a syringe protector according to at least one embodiment.
Figure 11:
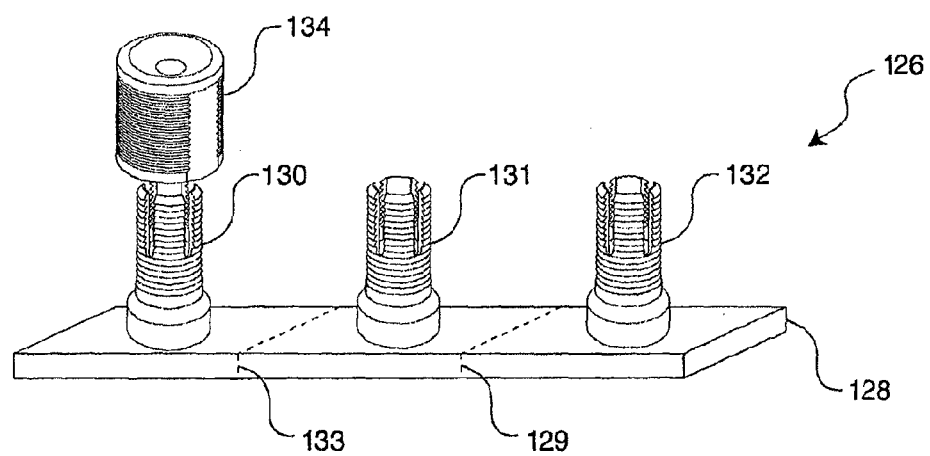
FIG. 11 is a perspective view of a syringe protector according to at least one embodiment.

FIG. 10 is a perspective view of still another embodiment of a syringe protector 112 comprising a tray 114 having four locking sites 116-119. In this particular embodiment, a syringe 120 is shown locked in a clamping member 122. Another clamping member 124 is shown in the "pre-loaded" configuration. FIG. 11 shows a perspective view of a further embodiment of a syringe protector 126. In this particular embodiment, a tray 128 includes a plurality of guard members 130-132 similar to guard member 70 as previously described with respect to FIG. 8, and includes an actuating member 134 similar to actuating member 68. Operation of protector 126 is similar to that of protector 66 as previously described. Optionally, once a syringe is locked in actuating member 134 and guard member 130, the syringe and guard/actuating member combination can be removed from tray 128 and disposed of using a traditional method (e.g., shredding or incineration) or placed in a conventional sharps container for later disposal. In one embodiment, the bases of guard members break away from the tray individually. In another embodiment, the tray is perforated such as by score lines 129, 133 so as to allow the removal of one or more guard members from the tray either individually or in groups as desired.

Figure 12:
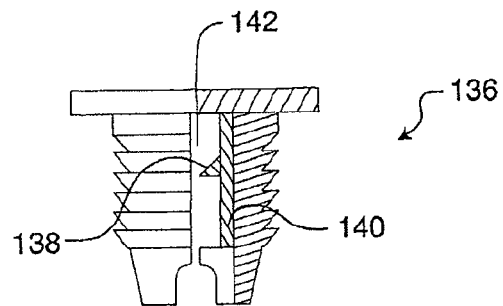
FIG. 12 is a partial cross-sectional view of a clamping member according to at least one embodiment.

An alternative clamping member 136 is shown in FIG. 12. In this particular embodiment, clamping member 136 includes at least one tooth or barb 138 disposed on the inner surface 140 of the axial passage 142. Barb 138 is configured and arranged such as to prevent a syringe inserted through axial passage 142 from being withdrawn from clamping member 136. In other embodiments of clamping members, the internal surface of the axial passage may include a greater number of barbs or barbs of different shapes, sizes and configurations.

Figure 13:
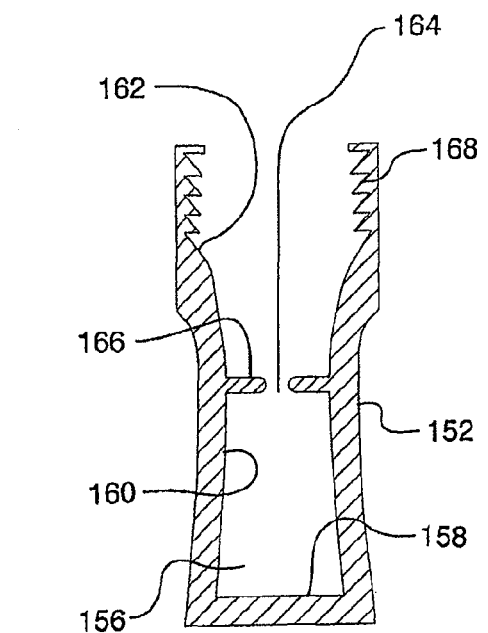
FIG. 13 is a partial cross-sectional view of a guard member according to at least one embodiment.

An alternative guard member 150 is shown in FIG. 13. In this particular embodiment, guard member 150 has an outer wall 152 and an inner wall 160 which defines a cavity 156 having a base 158. Guard member 150 further includes a threaded portion 168, a sloped deflecting surface 162, and a syringe stop member 166 attached to inner wall 160 and disposed in cavity 164 between deflecting surface 162 and base 158. In this particular embodiment, stop member 166 is an annular-shaped body having an opening 164 sized such that when a syringe is inserted in guard 150, a needle will pass through opening 164, but the nozzle an/or cylindrical body of the syringe will abut stop member 166. Further, stop member 166 is positioned such that when the syringe abuts stop member 166, the needle does not contact base 158, thereby preventing needle from accidentally being forced through base 158 by the application of too much force to the syringe. In other embodiments, the placement of stop member 166 is determined by the type and size of syringe used. In other embodiments, another configuration of a stop member or abutting surface is used such as a narrowing of the guard cavity.

At least one embodiment of a syringe protector according to the present disclosure is shown in FIGS. 14-24. Syringe protector 180 according to at least one embodiment of the present disclosure comprises needle guard 200, clamping member 250, and retaining member 300. As shown in the cross-sectional view of syringe protector 180 shown in FIG. 14, clamping member 250 is within needle guard 200, and retaining member 300 is within clamping member 250.

Figure 16:
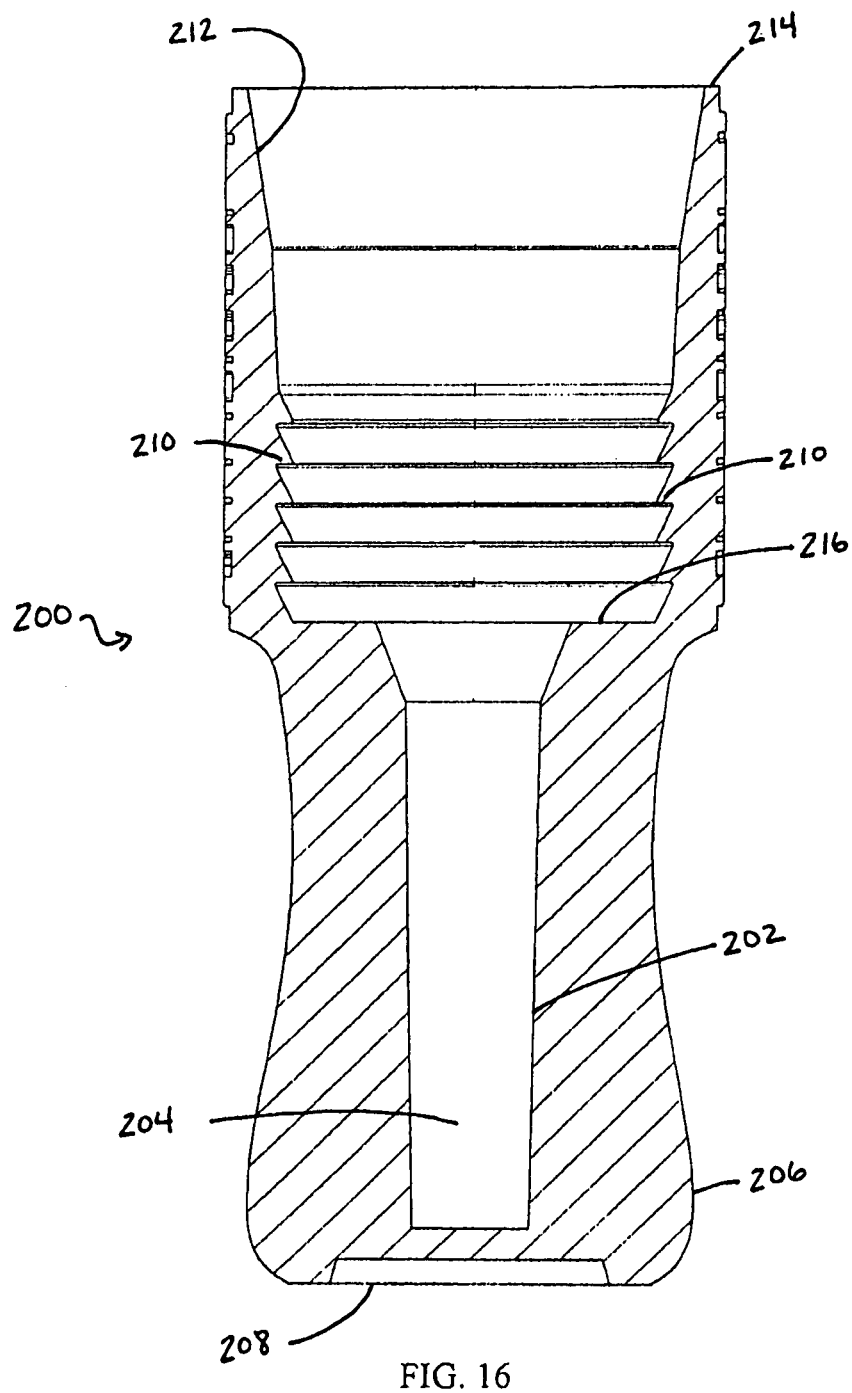
FIG. 16 is a plan view of a partial cross-section of the needle guard of FIG. 14, according to at least one embodiment.

Referring now to FIG. 16, there is shown a cross-sectional view of an embodiment of needle guard 200. As shown in the cross-sectional view of this embodiment of needle guard 200, needle guard 200 is generally tubular-shaped having interior wall 202 defining cavity 204. Needle guard 200 also comprises base 206 having generally flat bottom surface 208, toothed interior surface 210, internal surface 212, upper edge 214, and ledge 216. Internal surface 212 slopes between upper edge 214 and toothed interior surface 210.

Figure 17:
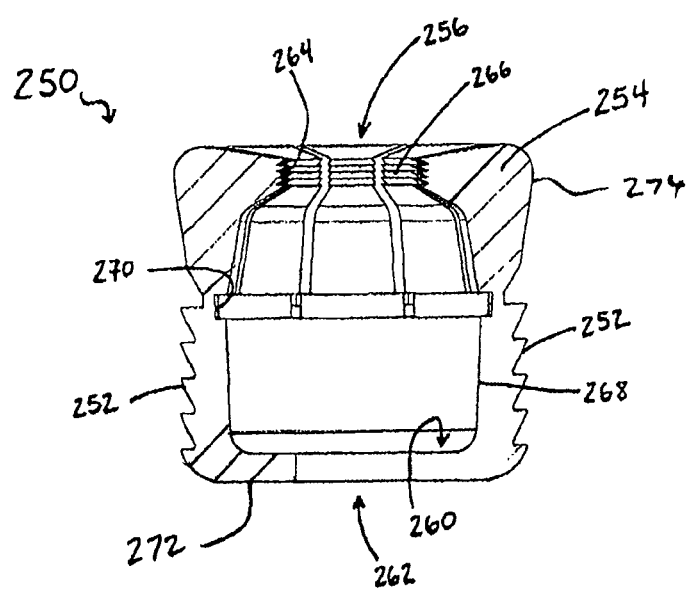
FIG. 17 is a plan view of a partial cross-section of the clamping member of FIG. 14, according to at least one embodiment.
Figure 18:
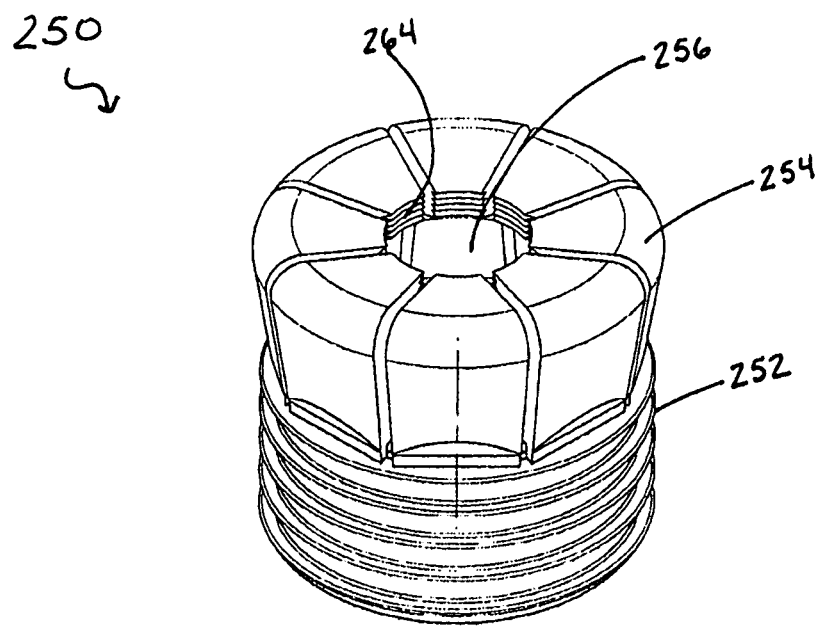
FIG. 18 is a perspective view of the clamping member of FIG. 14, according to at least one embodiment.

FIGS. 17-18 show cross-sectional and perspective views, respectively, of an embodiment of clamping member 250. According to at least this embodiment, clamping member 250 is substantially ferrule-shaped, and includes a toothed exterior surface 252, one or more flexible flanges 254 defining a first axial passage 256, a base wall 260 defining a second axial passage 262, and a lower surface 272. Each flexible flange 254 comprises a shoulder 274. In at least one embodiment, the interior of clamping member 250 is substantially hollow, with interior walls 268 defining a recess 270 sized to accommodate retaining member 300.

In at least one embodiment, clamping member 250 comprises eight (8) flexible flanges 254. Other embodiments may have a greater or lesser number of flexible flanges. In at least one embodiment, flexible flange 254 is comprised of a material having flexible properties, such as a plastic material or a thin metal material. Each flexible flange 254 comprises an inner wall 264. Optionally, one or more inner walls 264 includes one or more ribs or ridges 266.

Figure 15:
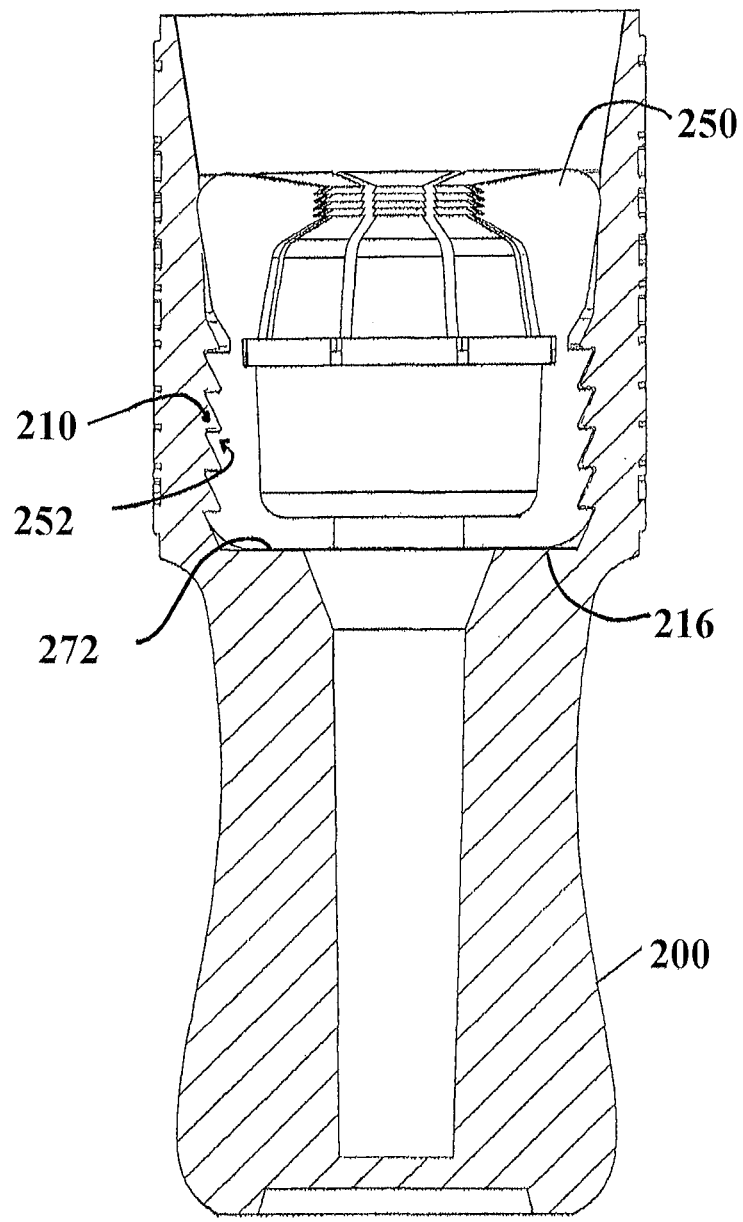
FIG. 15 is a plan view of a partial cross-section of the syringe protector of FIG. 14, according to at least one embodiment.

Referring now to FIG. 15, there is shown a cross-sectional view of clamping member 250 within needle guard 200 according to at least one embodiment of the present disclosure. In such an embodiment, toothed surface 252 and toothed surface 210 are configured and arranged such that when clamping member 250 is inserted into guard member 200, interaction between the toothed surfaces locks the two members together, as shown in FIG. 15. In at least one embodiment of syringe protector 180, at least one chamfer of exterior toothed surface 252 of clamping member 250 and at least one chamfer of interior toothed surface 210 of guard member 200 are disposed at approximately a complementary angle relative to the sides of clamping member 250 and guard member 200, respectively. In at least one embodiment, all chamfers of exterior toothed surface 252 of clamping member 250 and interior toothed surface 210 of guard member 200 are disposed at approximately a 45 degree angle relative to the sides of clamping member 250 and guard member 200, respectively.

Figure 14:
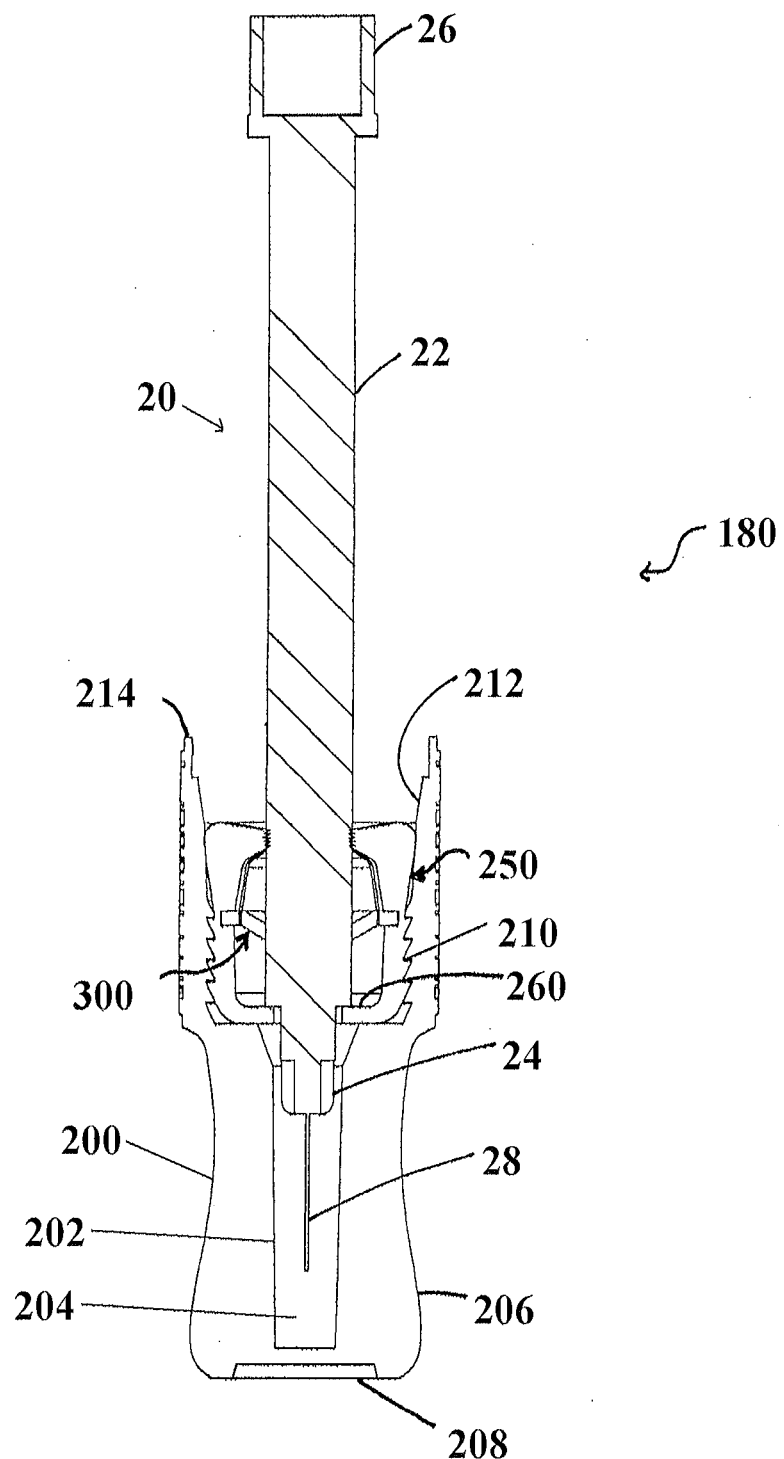
FIG. 14 is a plan view of a partial cross-section of a syringe protector with a syringe, according to at least one embodiment.

As also shown in FIG. 14-15, in at least one embodiment of syringe protector 180, clamping member 250 may be engaged with guard member 200 by inserting clamping member 250 through the opening defined by upper edge 214 so that flexible flanges 254 are in contact with internal surface 212. In at least one embodiment, shoulder 274 of each flexible flange 254 abuts internal surface 212.

Figure 19:
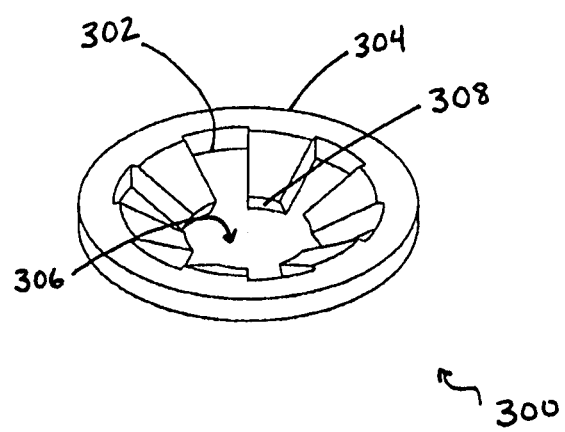
FIG. 19 is a perspective view of the retaining member of FIG. 14, according to at least one embodiment.
Figure 20:
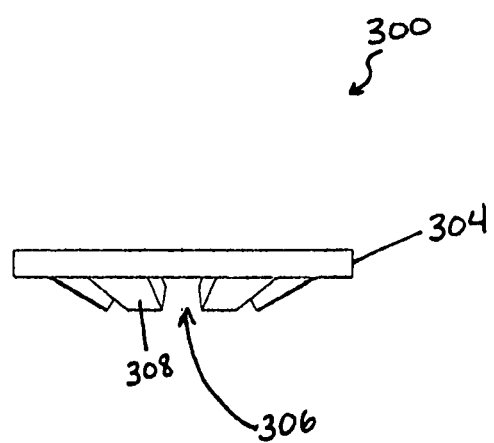
FIG. 20 is a perspective view of the retaining member of FIG. 14, according to at least one embodiment.
Figure 21:
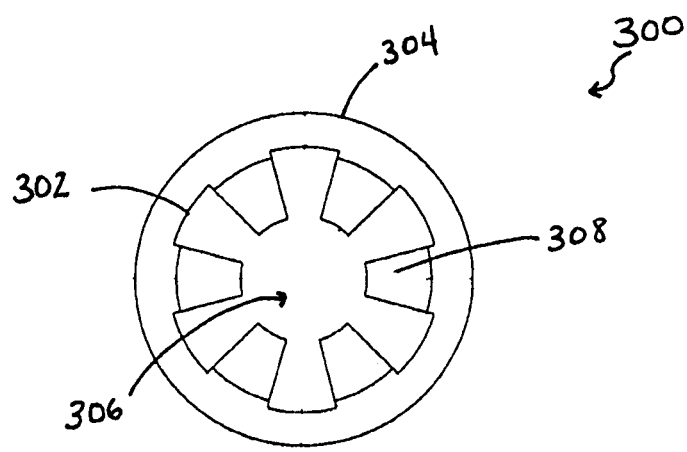
FIG. 21 is a perspective view of the retaining member of FIG. 14, according to at least one embodiment.

Referring now to FIGS. 19-21, shown are multiple views of at least one embodiment of retaining member 300. As shown in FIGS. 19-21, retaining member 300 is a ring-like structure having a retaining wall 302 and exterior wall 304. Retaining wall 302 is structured so as to define an opening 306. In at least one embodiment, retaining wall 302 is sized and structured in such a manner as to allow the unidirectional insertion of syringe 20 through opening 306. In at least one additional embodiment, retaining member 300 has at least one protrusion 308 extending from retaining wall 302. In at least one embodiment, the at least one protrusion 308 discourages the removal of syringe 20 once inserted.

Referring back to FIG. 14, in at least one embodiment, retaining member 300 is securably attached within clamping member 250 prior to insertion of syringe 20. The site of attachment of retaining member 300 may be at any point on clamping member 250 whereby the opening 306 of retaining member 300 is in line with first axial passage 256 and second axial passage 262. Achieving the attachment of retaining member 300 to clamping member 250 may be accomplished through any available process such as, for example, core molding.

In at least one embodiment, the interior diameter of the first axial passage 256 of clamping member 250 is sized such that it may receive the nozzle end 24 of a syringe 20 therethrough, as shown in FIG. 14. Continued urging of nozzle end 24 allows for the second axial passage 262 to receive nozzle end 24. Further urging of nozzle end 24 will produce a seatable engagement between the syringe 20 and base wall 260. In at least one embodiment, nozzle end 24 passes through opening 306 of retaining member 300 between the first axial passage 256 and second axial passage 262. When syringe 20 is engaged and seated in syringe guard 180, needle 28 is protectively surrounded by needle guard 200, thereby preventing accidental needle sticks until the syringe and guard combination is properly disposed of using mechanical shredding, incineration, and/or other suitable disposal means. Inner walls 264 of clamping member 250 and protrusions 308 of retaining member 300 frictionally engage the outer surface of cylindrical housing 22, impeding the removal of syringe 20 from syringe protector 180.

Figure 22:
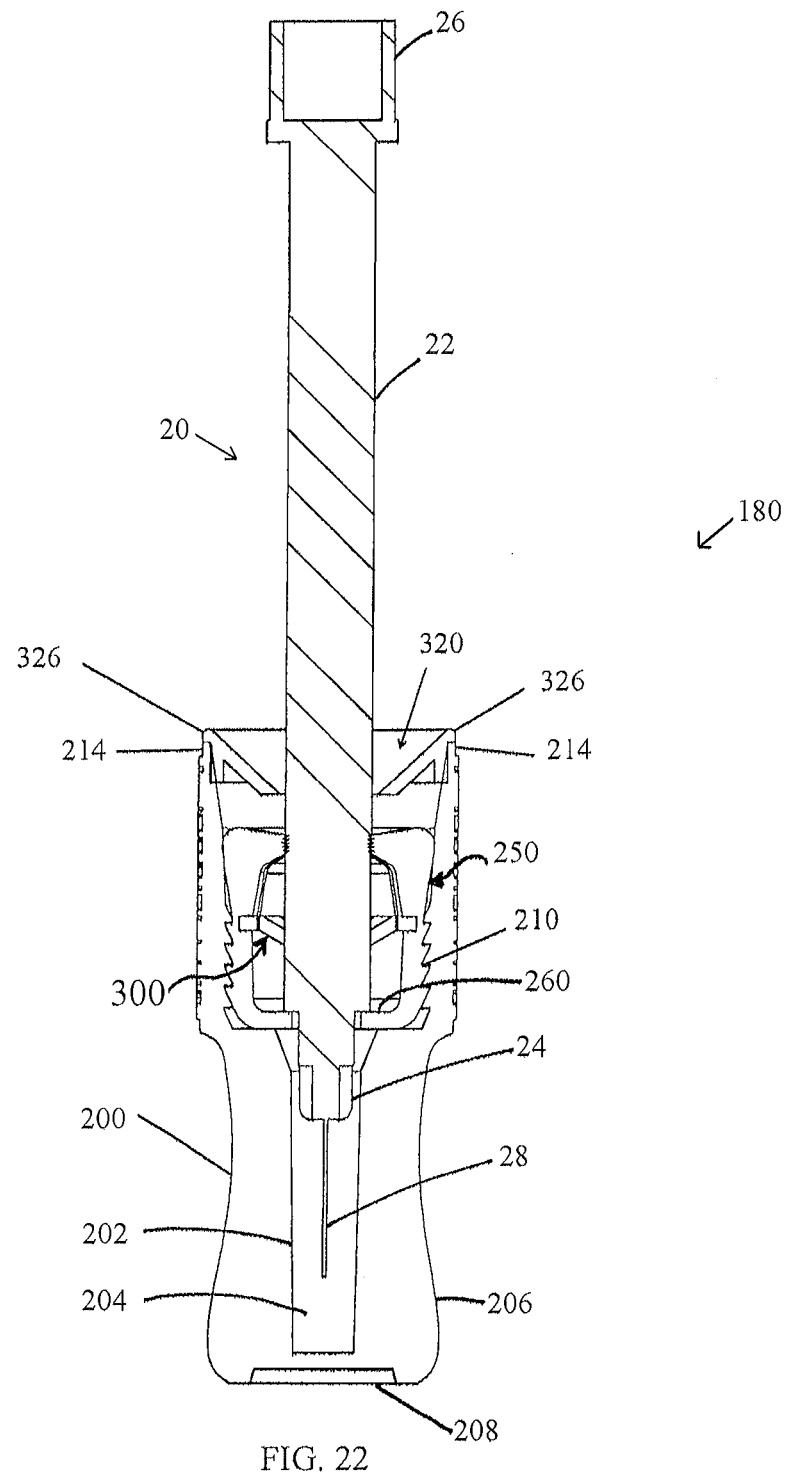
FIG. 22 is a plan view of a partial cross-section of a syringe protector with a syringe, according to at least one embodiment.

Referring now to FIG. 22, there is shown at least one embodiment of a syringe protector 180 is shown. Syringe protector 180 according to the present disclosure comprises a needle guard 200, a clamping member 250, a retaining member 300, and a cap 320.

Figure 23A:
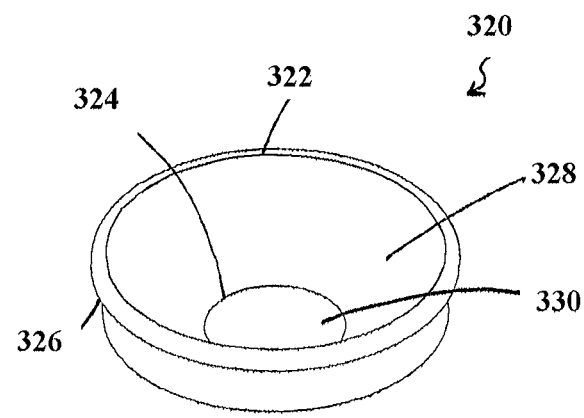
FIG. 23A is a perspective view of the cap of FIG. 14, according to at least one embodiment.
Figure 23B:
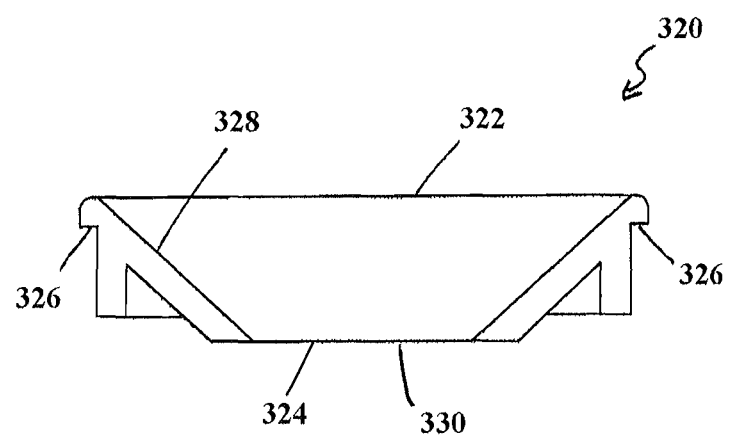
FIG. 23B is a cross-sectional view of the cap of FIG. 14, according to at least one embodiment.

FIGS. 23A-B show perspective and cross-sectional views, respectively, of at least one embodiment of cap 320. As shown in FIGS. 23A-B, cap is generally tubular shaped comprising a top rim 322 and a bottom rim 324 defining axial passage 330. Cap 320 further comprises an interior cap surface 328 between top rim 322 and bottom rim 324, and a cap ridge 326 positioned on the outer surface of top rim 322. In at least one embodiment, bottom rim 324 has a smaller diameter than top rim 322, causing interior cap surface 328 to have a slant. The slanting of cap surface 328 facilitates the insertion of needle 28 through axial passage 330. Cap ridge 326 is sized and shaped to rest on upper rim 214. The interaction between cap ridge 326 and upper rim 214 is such that cap 320 is fixed in place atop upper rim 214.

Figure 24:
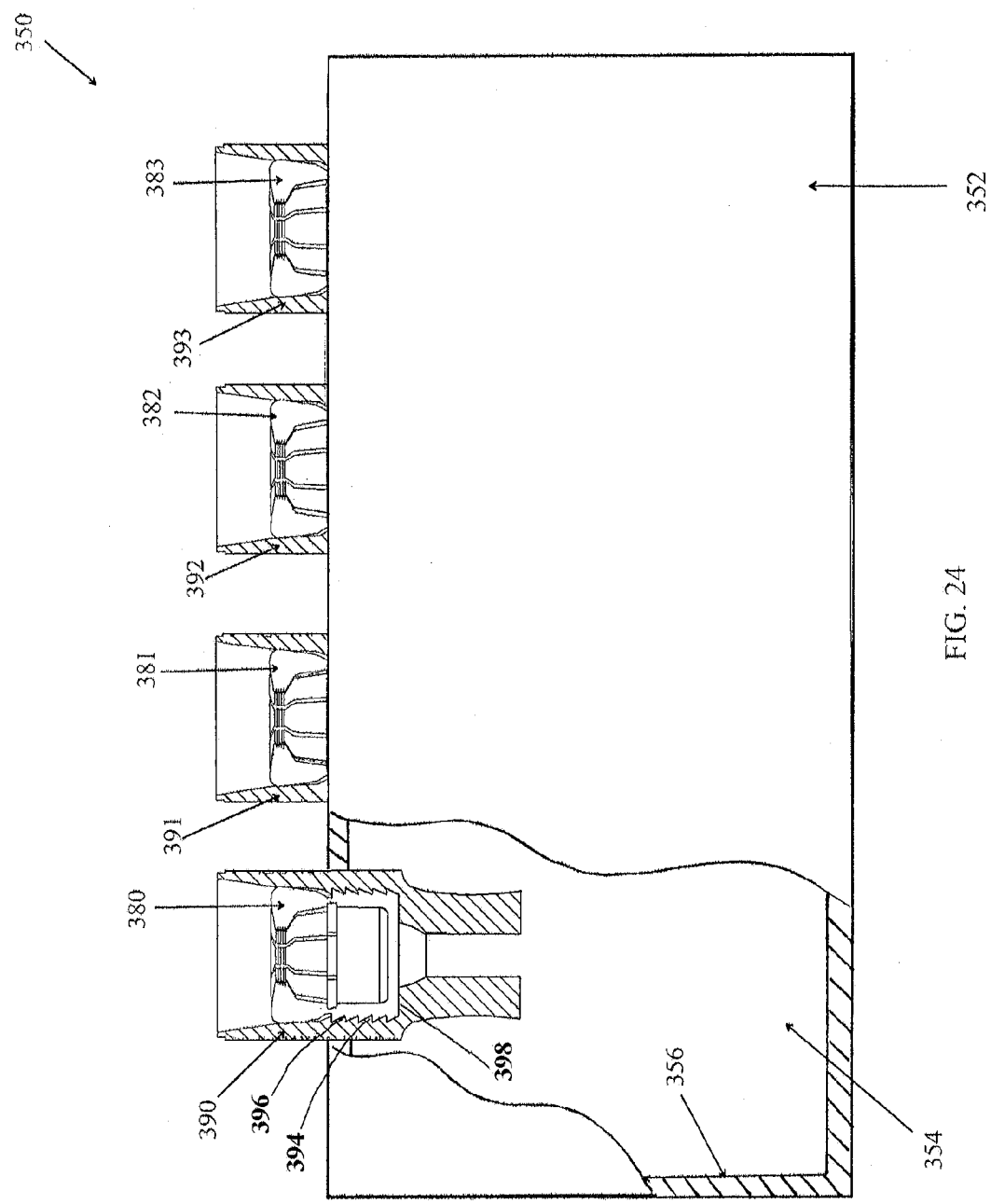
FIG. 24 is a side plan view of a partial cross-section of a syringe protector according to at least one embodiment.

A side plan view of a partial cross-section of syringe protector 350 according to at least one embodiment of the present disclosure is shown in FIG. 24. In this embodiment, syringe protector 350 comprises a box or tray 352 and a plurality of clamping members 380-383. Tray 352 is shown as a box having a cavity 354 bounded on one side by a substantially flat surface 356 having a plurality of locking site openings 390-393. In this particular embodiment, tray 352 includes four locking sites, but trays having a greater of lesser number of locking sites are also contemplated. Locking site 390 includes a toothed surface 392 having a plurality of teeth or ridges 394 and a stop ridge 396 to arrest downward movement of clamping member 380. In at least this embodiment, locking sites 390-393 are sized and adapted to accept clamping members of similar size and configuration. In additional embodiments, the tray includes locking sites configured and adapted to accept clamping members designed to clamp and hold syringes of different sizes and/or configurations.

While some embodiments of the disclosure have been illustrated and described in detail in the drawings and foregoing description, the same is to be considered as illustrative and not restrictive in character. It is understood that one of ordinary skill in the art could readily make a nigh-infinite number of insubstantial changes and modifications to the above-described embodiments, and that it would be impractical to attempt to describe all such variations in the present specification. Accordingly, it is understood that all changes and modifications that come within the spirit of the disclosure are desired to be protected.

I claim:

1. A syringe protector for enclosing a needle portion of a syringe, the syringe protector comprising:
    a clamping member having a toothed surface, a base wall, a first axial passage, a second axial passage, and at least one flexible flange, wherein said at least one flexible flange defines said first axial passage and said base wall defines said second axial passage;
    a retaining member operably connected to said clamping member and axially aligned with said first axial passage and said second axial passage, said retaining member having a plurality of inwardly oriented protrusions; and
    a needle guard having a toothed surface, said needle guard surrounding said clamping member, said clamping member moveable in one direction within said needle guard, wherein when said clamping member is moved within said needle guard an interaction between said toothed surface of said clamping member and said toothed surface of said needle guard increasingly securably engages said clamping member and said needle guard and an interaction between said at least one flexible flange and said needle guard increasingly deflects said at least one flexible flange.

2. The syringe protector of claim 1, wherein said toothed surface of said clamping member is an exterior surface and said toothed surface of said needle guard is an interior surface.

3. The syringe protector of claim 1, wherein said first axial passage of said clamping member further includes a plurality of ridges.

4. The syringe protector of claim 1, wherein said second axial passage is adapted to receive at least a portion of a syringe therethrough, wherein said syringe comprises a body having a needle attached to one end thereof, and wherein said needle guard further comprises a stop member configured and arranged so as to allow said needle to pass therethrough and to prevent said body from passing therethrough.

5. The syringe protector of claim 1, wherein at least one protrusion of said retaining member is oriented away from said first axial opening.

6. The syringe protector of claim 1, wherein said retaining member is operably connected to said clamping member between said first axial passage and said second axial passage.

7. The syringe protector of claim 1, wherein said retaining member is operably connected to said clamping member within said clamping member.

8. The syringe protector of claim 1, wherein said needle guard further comprises an upper edge and an internal surface between said upper edge and said toothed surface, said internal surface having a first diameter adjacent to said upper edge and a second diameter adjacent to said toothed surface, said first diameter being larger than said second diameter.

9. The syringe protector of claim 8, wherein said at least one flexible flange comprises a shoulder, said shoulder abutting said internal surface of said needle guard.

10. The syringe protector of claim 1, wherein said needle guard further comprises a cavity, said cavity sized to receive a needle portion of said syringe therein.

11. The syringe protector of claim 1, further comprising:
    a cap connected to said needle guard, said cap comprising an upper rim defining a first opening, and lower rim defining a second opening, and a continuous cap surface between said upper rim and lower rim.

12. The syringe protector of claim 11, wherein said first opening is larger than said second opening.

13. The syringe protector of claim 1, wherein said clamping member includes at least four flexible flanges.

14. The syringe protector of claim 1, wherein said retaining member has at least three protrusions.

15. A syringe protector for enclosing a needle portion of a syringe, the syringe protector comprising:
    a clamping member having an exterior toothed surface, at least one flexible flange, a first axial passage, and a second axial passage adapted to receive at least a portion of a syringe therethrough, the syringe comprising a syringe housing and a needle operably coupled to the syringe housing;
    a retaining member having a retaining wall defining an opening, said retaining wall further comprising at least one protrusion, wherein said retaining member is operably connected to said clamping member in such an arrangement as to maintain said opening of said retaining member between and in registration with said first axial passage and second axial passage; and
    a needle guard having an interior toothed surface, said clamping member moveable in one direction within said needle guard, wherein when said clamping member is moved within said needle guard interaction between said exterior toothed surface of said clamping member and said interior toothed surface of said needle guard lockably engages said clamping member and said guard member, said at least one protrusion of said retaining member compressively grips the syringe housing inserted through said opening of said retaining member to secure the syringe within the retaining member, and an interaction between said at least one flexible flange and said needle guard increasingly deflects said at least one flexible flange.

16. The syringe protector of claim 15, wherein said needle guard further comprises a cavity, said cavity sized to receive a needle portion of said syringe therein.

17. The syringe protector of claim 15, wherein said clamping member includes at least four flexible flanges.

18. A syringe protector for enclosing said needle portion of a syringe, the syringe protector comprising:
- a needle guard, said needle guard comprising a bottom end and a top end, said bottom end comprising a generally flat surface, said top end comprising an upper edge defining an opening at said top end, and said needle guard further comprising an internal chamber bounded by an internal surface, said internal surface comprising a first region adjacent said upper edge and a second region adjacent said first region, said first region and said second region arranged such that said first region is between said second region and said upper edge, said second region comprising a two or more internal teeth, said first region comprising a sloped surface such that a cross-sectional area of said internal chamber adjacent said upper edge is greater than a cross-sectional area of said internal chamber adjacent said second region;
- a clamping member, said clamping member comprising a first end, a first exterior section adjacent said first end, a second end, a second exterior section adjacent said second end, and an interior cavity, said first exterior section comprising two or more flexible flanges defining a first axial passage at said first end, said second exterior section comprising two or more exterior teeth and defining second axial passage at said second end; and
- a retaining member within said interior cavity; said retaining member comprising two or more protrusions extending into said interior cavity and defining a gap therebetween, said gap being in registration with said first axial passage and second axial passage, said two or more protrusions oriented in the direction of said second axial passage;
- wherein said clamping member is in said internal chamber of said needle guard, said first end of said clamping member oriented toward said top end of said needle guard, said second end of said clamping member oriented toward said bottom end of said needle guard, said two or more flexible flanges in contact with said first region of said internal surface, and said external teeth at least partially engaged with said internal teeth such that said clamping member cannot be removed from said needle guard, and
- wherein when pressure is exerted on said clamping member in the direction of said bottom end, said clamping member moves toward said bottom end thereby causing said external teeth to become more fully engaged with said internal teeth and said flexible flanges to be deformed by said first region of said internal surface such that a dimension of said first axial passage is reduced.

19. The syringe protector of claim 18, wherein said needle guard further comprises a cavity, said cavity sized to receive a needle portion of said syringe therein.

20. The syringe protector of claim 18, wherein said clamping member includes at least four flexible flanges.

* * * * *